(12) United States Patent
Tsai (10) Patent No.: US 12,310,565 B2
(45) Date of Patent: May 27, 2025

(54) VAGINAL SPECULUM

(71) Applicant: Yih-Chiou Tsai, Taichung (TW)

(72) Inventor: Yih-Chiou Tsai, Taichung (TW)

( * ) Notice: Subject to any disclaimer, the term of this patent is extended or adjusted under 35 U.S.C. 154(b) by 271 days.

(21) Appl. No.: 18/312,164

(22) Filed: May 4, 2023

(65) Prior Publication Data

US 2023/0293003 A1 Sep. 21, 2023

Related U.S. Application Data

(63) Continuation-in-part of application No. 17/700,021, filed on Mar. 21, 2022, now abandoned.

(51) Int. Cl.
*A61B 1/32* (2006.01)
*A61B 1/303* (2006.01)

(52) U.S. Cl.
CPC ............... *A61B 1/32* (2013.01); *A61B 1/303* (2013.01)

(58) Field of Classification Search
CPC .................................. A61B 1/32; A61B 1/303
See application file for complete search history.

(56) References Cited

U.S. PATENT DOCUMENTS 8,211,154 B2 * 7/2012 Fisher ............... A61B 17/8047
606/294
2020/0069171 A1 * 3/2020 Miller .................. A61B 1/0653

* cited by examiner

*Primary Examiner* — Tracy L Kamikawa
(74) *Attorney, Agent, or Firm* — RABIN & BERDO, P.C.

(57) ABSTRACT

A vaginal speculum has an upper member having a first handle, a lower member having a second handle, a threaded rod, and a nut. A positioning cavity is formed in the second handle and has an insertion cavity and multiple engaging grooves. A rod hole is formed through the second handle and communicates with the insertion cavity. Multiple ribs are formed between the rod hole and the engaging grooves. The threaded rod has a head, a rod, and multiple engaging protrusions. The head is mounted in the insertion cavity. The engaging protrusions are arranged around the head and respectively engaged with the engaging grooves. The rod extends from the head, through the rod hole, and toward the first handle. The nut is connected with the rod of the threaded rod via a threaded connection. Accordingly, the head of the threaded rod is firmly fixed in the positioning cavity.

9 Claims, 9 Drawing Sheets

VAGINAL SPECULUM

CROSS-REFERENCE TO RELATED APPLICATION

This present invention is a continuation-in-part application of application Ser. No. 17/700,021, filed on Mar. 21, 2022, which is incorporated herein by reference.

BACKGROUND OF THE INVENTION

1. Field of the Invention

The present invention relates to a disposable medical device, and more particularly to a vaginal speculum that has a threaded rod free from rotating relative to a handle thereof.

2. Description of Related Art

A conventional vaginal speculum substantially has an upper member, a lower member, a threaded rod, and a nut. The upper member and the lower member are pivotally connected with each other. Each of the upper and the lower members has a handle extending downwardly therefrom. The threaded rod is fixed in the handle of the lower member and extends toward and through the handle of the upper member. The nut is connected with the threaded rod via a threaded connection and selectively abuts against the handle of the upper member to limit a relative opening position of the upper and the lower members.

To prevent the threaded rod from rotating relative to the lower member during rotating the nut to adjust a position of the nut relative to the threaded rod, the threaded rod has a limiting surface formed in an annular surface of a head thereof, and the lower member has an insertion cavity corresponding to the head of the threaded rod in shape and in size and formed in the handle thereof. The head of the threaded rod is mounted in and engages with the insertion cavity to prevent the threaded rod from rotating relative to the lower member.

However, because the threaded rod and the lower member are made of plastic, the head of the threaded rod and the insertion cavity of the lower member are easily deformed via insertion molding. Consequently, the head of the threaded rod cannot be stably engaged with the insertion cavity of the lower member, the head of the threaded rod is easily disengaged from or separated from the insertion cavity, and the threaded rod is easily rotated relative to the lower member.

To overcome the shortcomings, the present invention provides a vaginal speculum to mitigate or obviate the aforementioned problems.

SUMMARY OF THE INVENTION

The main objective of the present invention is to provide a vaginal speculum having a rod firmly engaged in the handle of the lower member.

A vaginal speculum comprises an upper member, a lower member, a threaded rod, and a nut. The upper member has a first handle extending downwardly from the upper member. The lower member is pivotally connected with the upper member and has a second handle extending downwardly from the lower member, located at a side of the first handle, and having a first side surface that faces away from the first handle and a second side surface that faces toward the first handle. A positioning cavity is formed in the second handle and has an insertion cavity, multiple engaging grooves, a rod hole, and multiple ribs. The insertion cavity is recessed in the first side surface of the second handle and has an end surface away from the first side surface of the second handle spaced from the second side surface of the second handle and at least one cavity limiting surface defined in an annular surface of the insertion cavity.

The engaging grooves are arranged around the insertion cavity and are spaced from each other. Each of the engaging grooves has a side opening formed in the annular surface of the insertion cavity and communicating with the insertion cavity, an end surface near the first side surface of the second handle spaced from the first side surface of the second handle, and an end opening formed in the second side surface of the second handle. The rod hole is formed through the second side surface of the second handle of the end surface of the insertion cavity and communicates with the insertion cavity. Each of the multiple ribs is formed between the rod hole and a respective one of the multiple engaging grooves from the second side surface of the second handle to the end surface of the insertion cavity to separate the rod hole apart from the respective one of the engaging grooves. The threaded rod has a head, multiple engaging protrusions, and a rod. The head is mounted in the insertion cavity of the positioning cavity and has at least one head limiting surface defined in an annular surface of the head and corresponding to the at least one cavity limiting surface in position and shape. The engaging protrusions protrude from the annular surface of the head, are spaced from each other, and are respectively engaged with the engaging grooves of the positioning cavity. The rod extends from the head toward the first handle and extends through the rod hole in the second handle and the first handle. The nut is connected with the rod of the threaded rod via a threaded connection and selectively abuts against the first handle.

Other objects, advantages, and novel features of the invention will become more apparent from the following detailed description when taken in conjunction with the accompanying drawings.

DETAILED DESCRIPTION OF THE PREFERRED EMBODIMENTS

Figure 1:
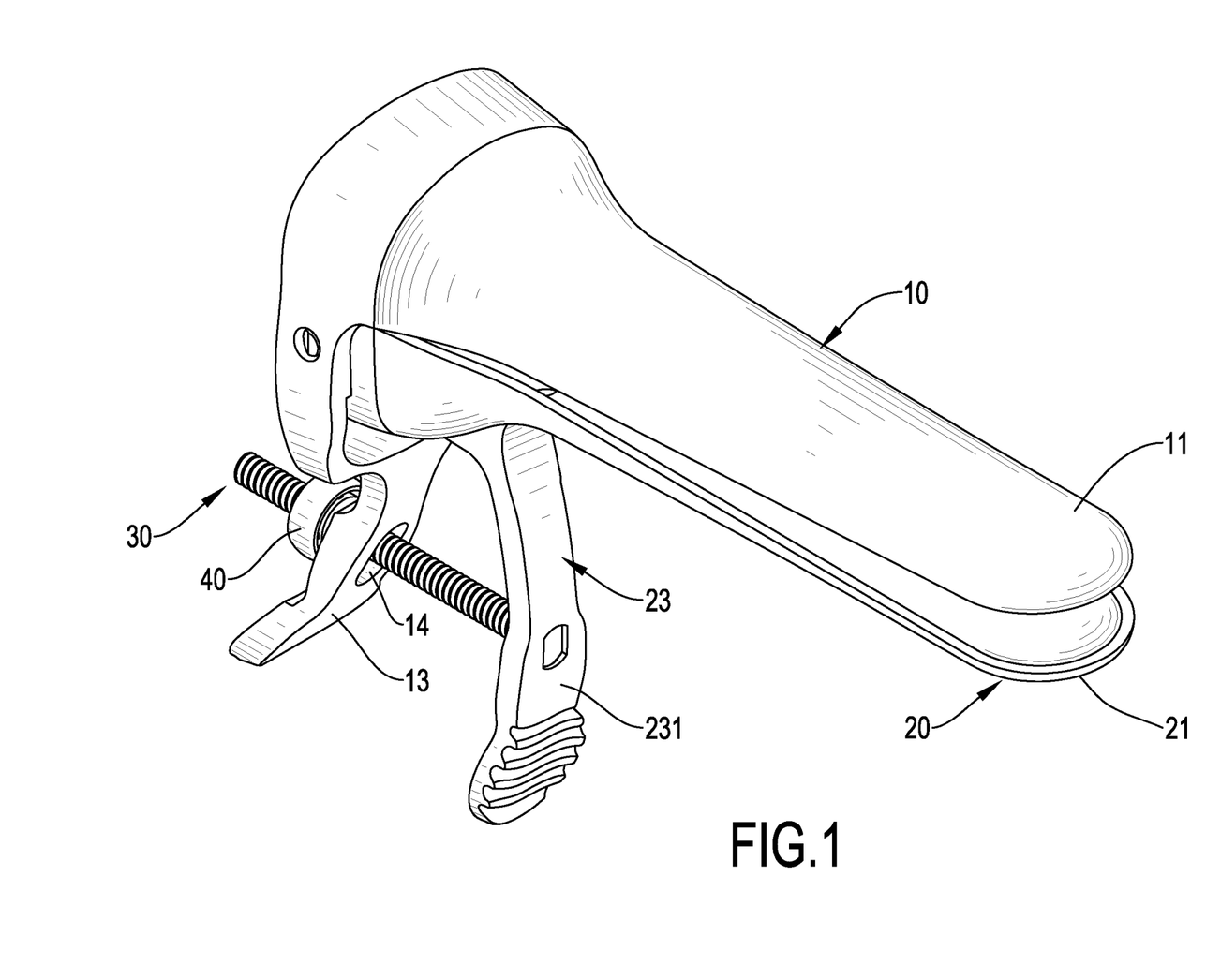
FIG. 1 is a perspective view of a vaginal speculum in accordance with the present invention.
Figure 2:
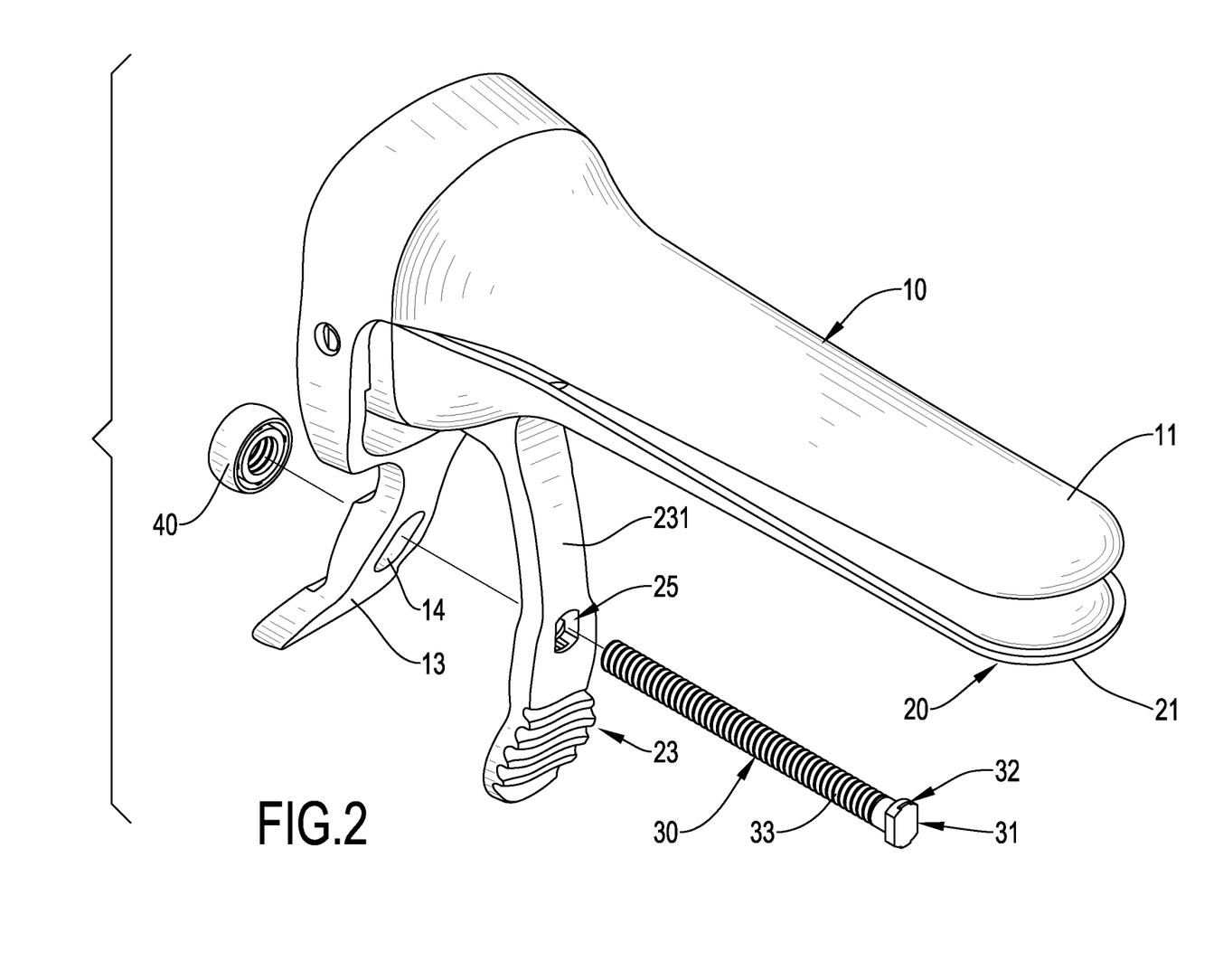
FIG. 2 is an exploded perspective view of the vaginal speculum in FIG. 1 before assembly.
Figure 3:
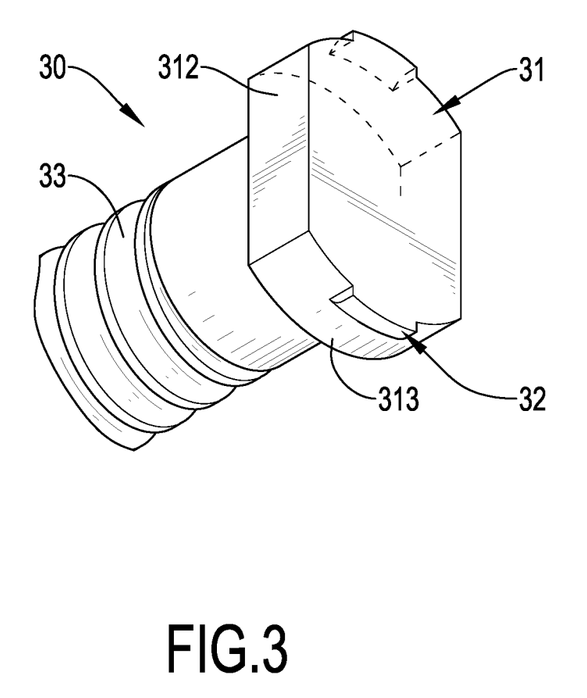
FIG. 3 is an enlarged perspective view of a threaded rod of the vaginal speculum in FIG. 1.

With reference to FIGS. 1 and 2, a vaginal speculum in accordance with the present invention has an upper member 10, a lower member 20, a threaded rod 30, and a nut 40. The upper member 10, the lower member 20, the threaded rod 30, and the nut 40 are made of plastic.

The upper member 10 and the lower member 20 are pivotally connected with each other. The upper member 10 has an upper blade 11 formed at a front side of the upper member 10, the lower member 20 has a lower blade 21 formed at a front side of the lower member 20, and the upper and the lower blades 11, 21 can be moved away from or toward each other. The upper member 10 has a first handle 13 extending downwardly from the upper member 10. The lower member 20 has a second handle 23 extending from the lower member 20 and located at a side of the first handle 13. In this embodiment, the second handle 23 is located in front of the first handle 13. The first handle 13 and the second handle 23 are held and pressed by a user to move relative to each other to drive the upper blade 11 and the lower blade 21 to open relative to each other.

With reference to FIGS. 2, 6 to 8, the second handle 23 has a first side surface 231 and a second side surface 232. The first side surface 231 faces away from the first handle 13. The second side surface 232 faces toward the first handle 13. A positioning cavity 25 is formed in the second handle 23. The positioning cavity 25 has an insertion cavity 252 and multiple engaging grooves 255. The insertion cavity 252 is recessed in the first side surface 231 of the second handle 23. An end surface of the insertion cavity 252 away from the first side surface 231 is spaced from the second side surface 232. The insertion cavity 252 has at least one cavity limiting surface 253 defined in an annular surface of the insertion cavity 252. The engaging grooves 255 are arranged around the insertion cavity 252 and are spaced from each other. Each of the engaging grooves 255 has a side opening formed in the annular surface of the insertion cavity 252 and communicating with the insertion cavity 252. An end surface of each of the engaging grooves 255 that faces toward the first side surface 231 of the second handle 23 is spaced from the first side surface 231 of the second handle 23. Preferably, each of the engaging grooves 255 has an end opening formed in the second side surface 232 of the second handle 23. A rod hole 24 is formed through the second side surface 232 of the second handle 23 and the end surface of the insertion cavity 252 and communicates with the insertion cavity 252. A diameter of a circumscribed circle of the rod hole 24 is smaller than a diameter of a circumscribed circle of the insertion cavity 252. Multiple ribs 27 are formed in the second handle 23. Each one of the multiple ribs 27 is formed between the rod hole 24 and a respective one of the engaging grooves 255 from the second side surface 232 of the second handle 23 to the end surface of the insertion cavity 252 to separate the rod hole 24 apart from the respective one of the engaging grooves 255.

With reference to FIGS. 2 to 5, and 8, the threaded rod 30 has a head 31, a rod 33, and multiple engaging protrusions 32. The head 31 is mounted in the insertion cavity 252 of the positioning cavity 25 and has at least one head limiting surface 312 defined in an annular surface of the head 31, corresponding to the at least one cavity limiting surface 253 in position and shape, and aligned with the at least one cavity limiting surface 253. The engaging protrusions 32 protrude from the annular surface of the head 31, are spaced from each other, and are respectively engaged with the engaging grooves 255 of the positioning cavity 25. The rod 33 extends from the head 31 toward the first handle 13 and extends through the second handle 23 and the first handle 13. A through hole 14 is formed through the first handle 13. The rod 33 of the threaded rod 30 extends through the rod hole 24 in the second handle 23 and the through hole 14 in the first handle 13 and extends out from the first handle 13.

With reference to FIGS. 1 and 2, the nut 40 is connected with the rod 33 of the threaded rod 30 via a threaded connection and selectively abuts against the first handle 13 to limit a relative open position of the first upper member 10 and the lower member 20.

In this embodiment, with reference to FIGS. 6 to 9, the insertion cavity 252 has two said cavity limiting surfaces 253 and two cavity arced surfaces 254 defined in the annular surface of the insertion cavity 252. The two cavity limiting surfaces 253 are spaced from each other. The two cavity arced surfaces 254 are connected with the two cavity limiting surfaces 253 and are arranged opposite to each other. The positioning cavity 25 has two said engaging grooves 255 being adjacent to the two cavity arced surfaces 254 respectively and communicating with the insertion cavity 252.

With reference to FIGS. 3 to 5, and 9, the head 31 of the threaded rod 30 has two said head limiting surfaces 312 and two head arced surfaces 313 defined in the annular surface of the head 31. The two head limiting surfaces 312 are respectively aligned with the two cavity limiting surfaces 253. The two head arced surfaces 313 are connected with the two head limiting surfaces 312, are arranged opposite to each other, and are respectively aligned with the two cavity arced surfaces 254. The threaded rod 30 has two said engaging protrusions 32 respectively protruding from the two head arced surfaces 313 and respectively engaged with the two engaging grooves 255.

Figure 4:
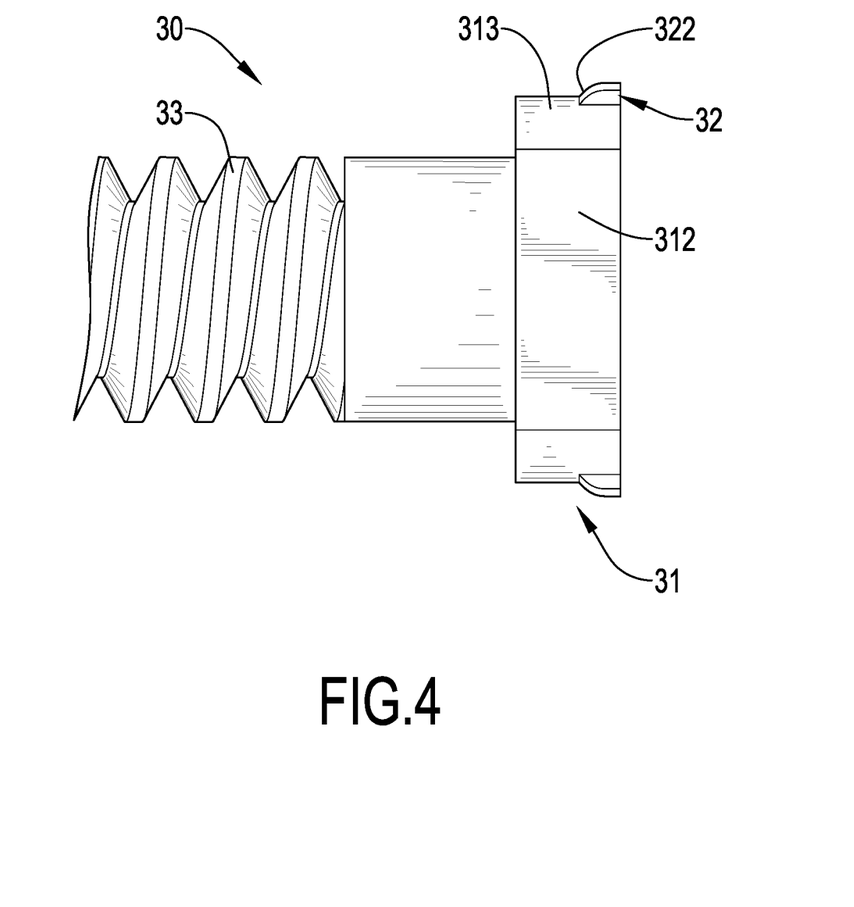
FIG. 4 is an enlarged side view of the threaded rod of the vaginal speculum in FIG. 3.
Figure 5:
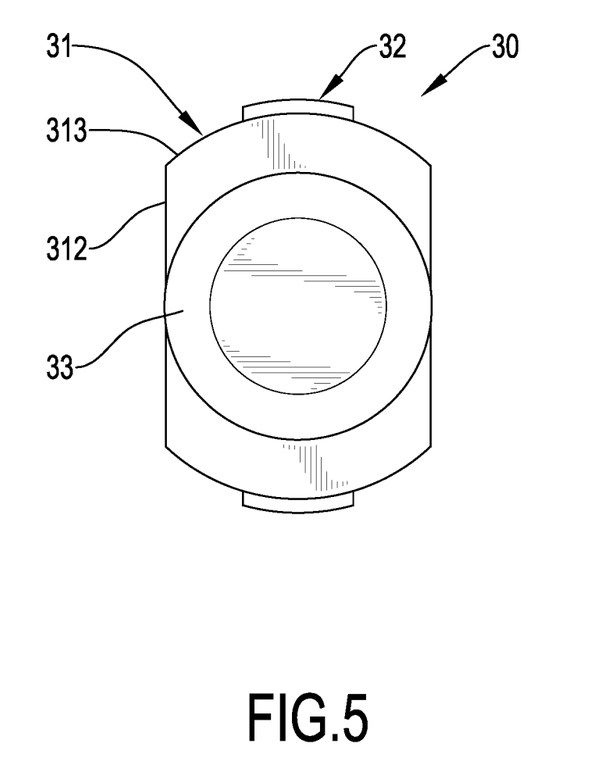
FIG. 5 is an enlarged end view of the threaded rod of the vaginal speculum in FIG. 3.
Figure 6:
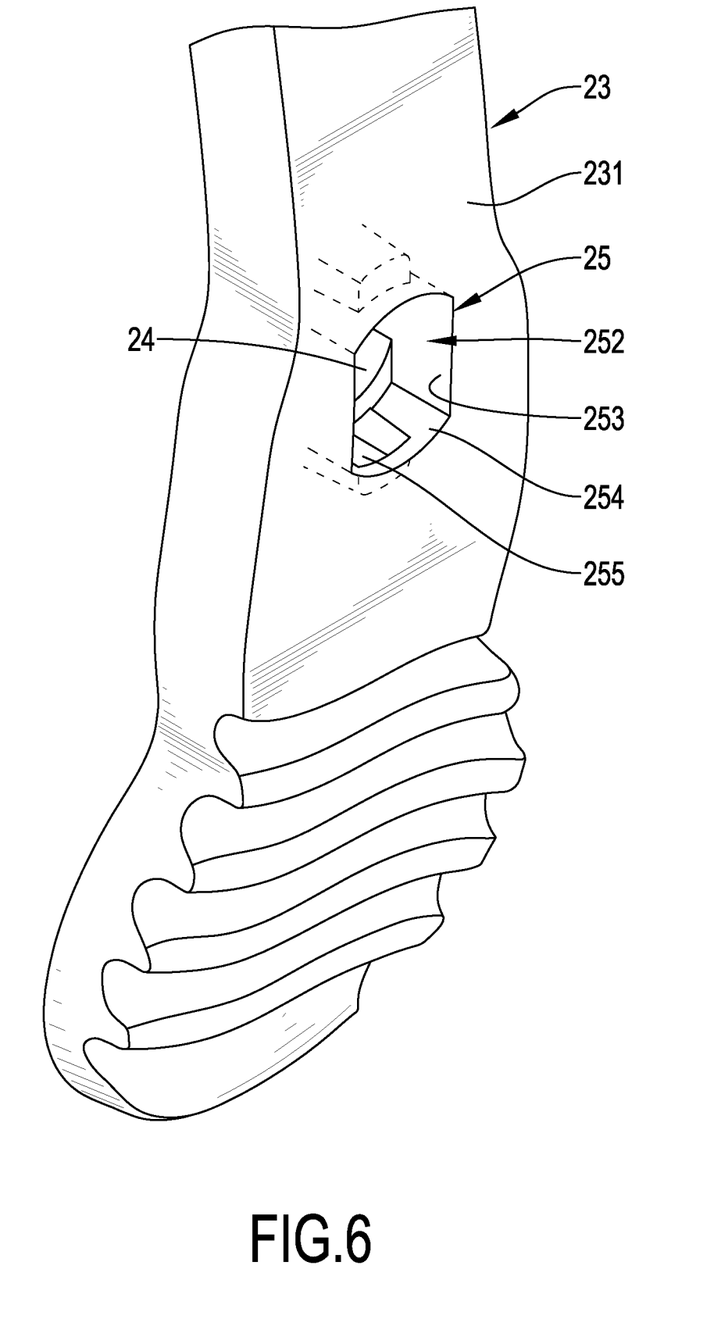
FIG. 6 is an enlarged perspective view of a lower member of the vaginal speculum in FIG. 1.
Figure 7:
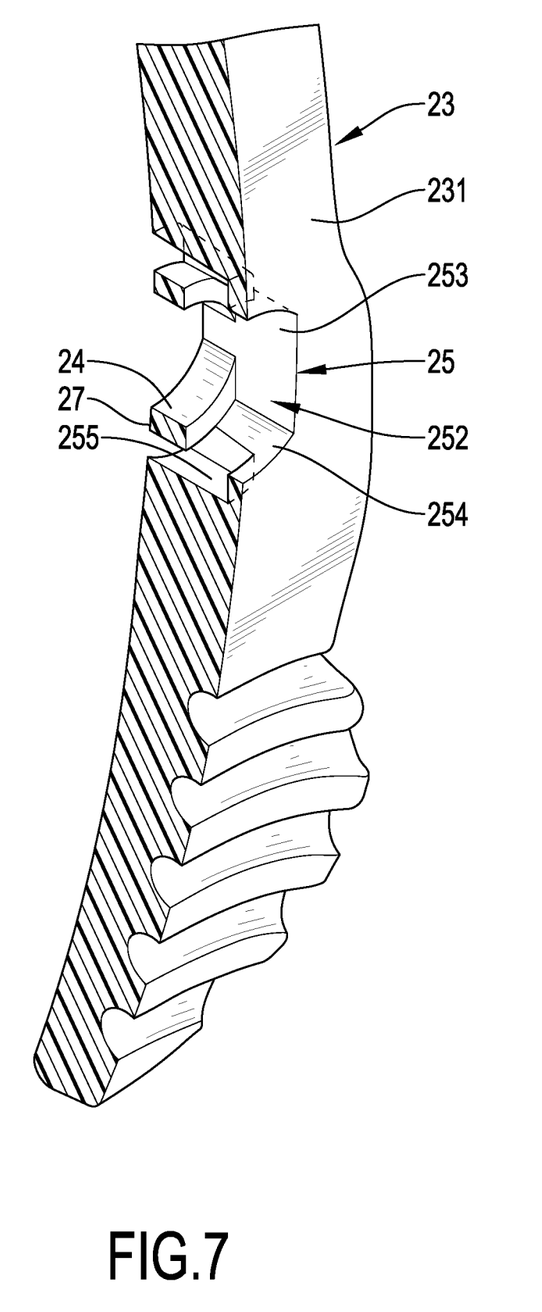
FIG. 7 is an enlarged perspective view in partial section of the lower member of the vaginal speculum in FIG. 6.
Figure 8:
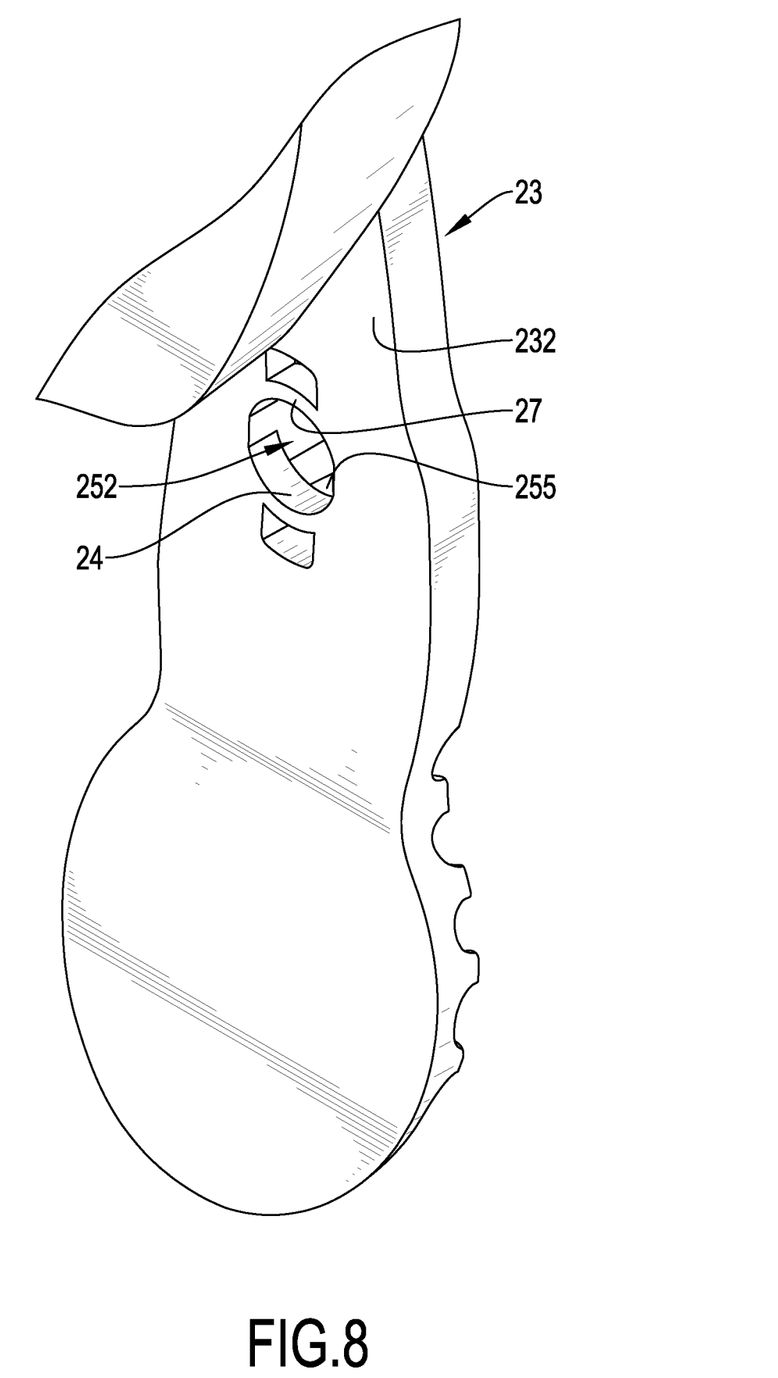
FIG. 8 is another enlarged perspective view of the lower member of the vaginal speculum in FIG. 6.

Preferably, as shown in FIG. 4, one of two ends of each of the engaging protrusions 32 that faces away from the rod 33 is aligned with one of two ends of the head 31 that faces away from the rod 33. A distance is formed between the other one of the two ends of each of the engaging protrusions 32 that faces toward the rod 33 and the other one of the two ends of the head 31 that faces toward the rod 33. A length of each of the engaging protrusions 32 is smaller than a length of the head 31. The length of each of the engaging protrusions 32 is smaller than or equal to ⅔ times of the length of the head 31 and is larger than or equal to ⅓ times of the length of the head 31.

Preferably, each of the engaging protrusions 32 has a guiding surface 322 defined in the end of the engaging protrusion 32 that faces toward the rod 33. The guiding surface 322 extends toward the rod 33 and gradually approaches the annular surface of the head 31. So the engaging protrusions 32 can be easily pressed into the insertion cavity 252.

Figure 9:
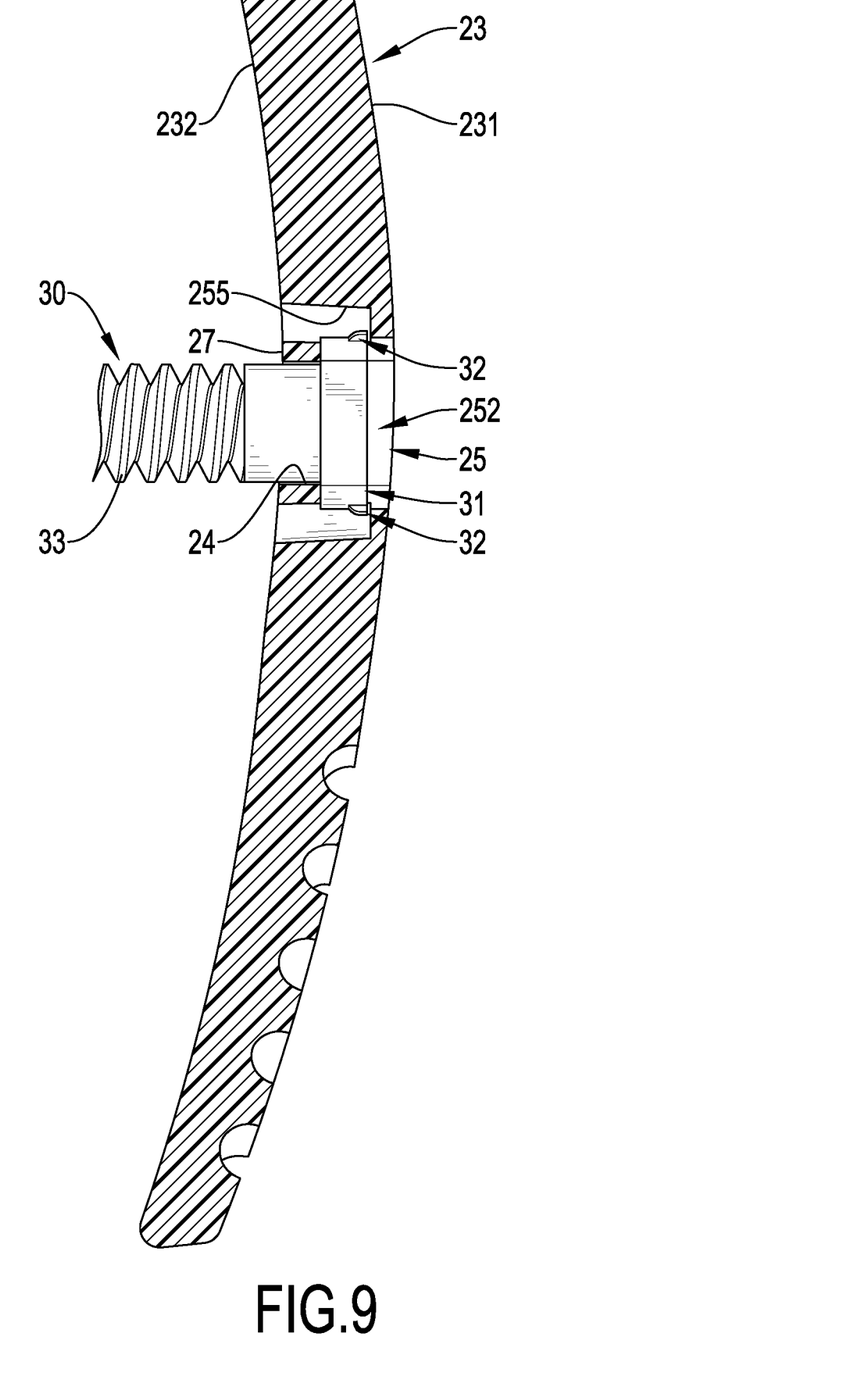
FIG. 9 is an enlarged side view in partial section of the vaginal speculum in FIG. 1.

With reference to FIGS. 2 and 9, to assemble the threaded rod 30, the rod 33 of the threaded rod 30 is inserted in the rod hole 24 in the second handle 23 from the first side surface 231, and the head 31 of the threaded rod 30 is pressed from the end thereof that faces away from the rod 33 to press the engaging protrusions 32 of the threaded rod 30 into the insertion cavity 252 and slide to engage with the engaging grooves 255 respectively. The end of the head 31 of the threaded rod 30 that faces toward the rod 33 is limited by the end surface of the insertion cavity 252, and the ends of the engaging protrusions 32 that faces away from the rod 33 are limited by the end surfaces of the engaging grooves 255 near the first side surface 231 of the second handle 23. So a longitudinal position of the threaded rod 30 relative to the second handle 23 is limited, and the threaded rod 30 will not be separated from the positioning cavity 25. As each one of the multiple engaging grooves 255 has the end opening formed in the second side surface 232 of the second handle 23 and is spaced apart from the rod hole 24 by one of the ribs 27, each one of the multiple engaging grooves 255 can be easily formed to communicate with the insertion cavity 252 and to be spaced apart from the first side surface 231 of the second handle 23 via extending the corresponding engaging groove 255 from the second side surface 232 toward the first side surface 231 of the second handle 23.

Moreover, because the head 31 of the threaded rod 30 has the head limiting surfaces 312 corresponding to the cavity limiting surfaces 253 of the insertion cavity 252 in shapes and positions, the threaded rod 30 is prevented from rotating relative to the second handle 23. With such arrangement, the threaded rod 30 can be easily mounted in the second handle 23, and the head 31 of the threaded rod 30 can be easily, firmly, and stably fixed in the positioning cavity 25 in the second handle 23 to prevent the thread rod 30 from separating from the positioning cavity 25 and from longitudinally sliding relative to the second handle 23.

Accordingly, the vaginal speculum of the present invention has simplified structure, and can be easily manufactured at lower cost. The threaded rod 30 can be firmly and stably fixed in the second handle 23 in position without longitudinally sliding, separating from the second handle 23, and shaking relative to the second handle 23, thereby reducing noise and enhancing the product quality and operation quality.

What is claimed is:

1. A vaginal speculum comprising:
   an upper member having a first handle extending downwardly from the upper member;
   a lower member pivotally connected with the upper member and having
      a second handle extending downwardly from the lower member, located at a side of the first handle, and having a first side surface facing away from the first handle and a second side surface facing toward the first handle; and
      a positioning cavity formed in the second handle and having
         an insertion cavity recessed in the first side surface of the second handle and having an end surface away from the first side surface of the second handle spaced from the second side surface of the second handle and at least one cavity limiting surface defined in an annular surface of the insertion cavity;
         multiple engaging grooves arranged around the insertion cavity and spaced from each other, and each of the multiple engaging grooves having
            a side opening formed in the annular surface of the insertion cavity and communicating with the insertion cavity;
            an end surface near the first side surface of the second handle spaced from the first side surface of the second handle; and
            an end opening formed in the second side surface of the second handle;
         a rod hole formed through the second side surface of the second handle and the end surface of the insertion cavity and communicating with the insertion cavity; and
         multiple ribs, each of the multiple ribs formed between the rod hole and a respective one of the multiple engaging grooves from the second side surface of the second handle to the end surface of the insertion cavity to separate the rod hole apart from the respective one of the multiple engaging grooves;
   a threaded rod having
      a head mounted in the insertion cavity of the positioning cavity and having
         at least one head limiting surface defined in an annular surface of the head and corresponding to the at least one cavity limiting surface in position and shape;
         multiple engaging protrusions protruding from the annular surface of the head, spaced from each other, and each configured to respectively engage with a respective one of the multiple engaging grooves of the positioning cavity; and
      a rod extending from the head toward the first handle and extending through the rod hole in the second handle and the first handle; and
   a nut connected with the rod of the threaded rod via a threaded connection and selectively abutting against the first handle.

2. The vaginal speculum as claimed in claim 1, wherein each of the multiple engaging protrusions has a guiding surface defined in one of two ends of the respective one of the multiple engaging protrusions facing toward the rod.

3. The vaginal speculum as claimed in claim 2, wherein the other one of the two ends of the respective one of the multiple engaging protrusions facing away from the rod is aligned with one of two ends of the head facing away from the rod, and a distance is formed between the one of the two ends of the respective one of the multiple engaging protrusions facing toward the rod and the other one of the two ends of the head facing toward the rod.

4. The vaginal speculum as claimed in claim 3, wherein
   the insertion cavity has two of the at least one cavity limiting surface and two cavity arced surfaces defined in the annular surface of the insertion cavity, the two cavity limiting surfaces are spaced from each other, and the two cavity arced surfaces are connected with the two cavity limiting surfaces and are arranged opposite to each other;
   the positioning cavity has two of the multiple engaging grooves being adjacent to the two cavity arced surfaces respectively and communicating with the insertion cavity;
   the head of the threaded rod has two of the at least one head limiting surface and two head arced surfaces, the two head limiting surfaces are respectively aligned with the two cavity limiting surfaces, and the two head arced surfaces are connected with the two head limiting surfaces, are arranged opposite to each other, and are respectively aligned with the two cavity arced surfaces; and
   the threaded rod has two of the multiple engaging protrusions respectively protruding from the two head arced surfaces and respectively engaged with the two engaging grooves.

5. The vaginal speculum as claimed in claim 4, wherein
   a diameter of a circumscribed circle of the rod hole is smaller than a diameter of a circumscribed circle of the insertion cavity;
   a through hole is formed through the first handle; and
   the rod of the threaded rod extends through the through hole in the first handle and extends out from the first handle.

6. The vaginal speculum as claimed in claim 2, wherein
   the insertion cavity has two of the at least one cavity limiting surface and two cavity arced surfaces defined in the annular surface of the insertion cavity, the two cavity limiting surfaces are spaced from each other, and the two cavity arced surfaces are connected with the two cavity limiting surfaces and are arranged opposite to each other;

the positioning cavity has two of the multiple engaging grooves being adjacent to the two cavity arced surfaces respectively and communicating with the insertion cavity;

the head of the threaded rod has two of the at least one head limiting surface and two head arced surfaces, the two head limiting surfaces are respectively aligned with the two cavity limiting surfaces, and the two head arced surfaces are connected with the two head limiting surfaces, are arranged opposite to each other, and are respectively aligned with the two cavity arced surfaces; and the threaded rod has two of the multiple engaging protrusions respectively protruding from the two head arced surfaces and respectively engaged with the two engaging grooves.

7. The vaginal speculum as claimed in claim 6, wherein
a diameter of a circumscribed circle of the rod hole is smaller than a diameter of a circumscribed circle of the insertion cavity;
a through hole is formed through the first handle; and
the rod of the threaded rod extends through the through hole in the first handle and extends out from the first handle.

8. The vaginal speculum as claimed in claim 1, wherein the insertion cavity has two of the at least one cavity limiting surface and two cavity arced surfaces defined in the annular surface of the insertion cavity, the two cavity limiting surfaces are spaced from each other, and the two cavity arced surfaces are connected with the two cavity limiting surfaces and are arranged opposite to each other;

the positioning cavity has two of the multiple engaging grooves being adjacent to the two cavity arced surfaces respectively and communicating with the insertion cavity;

the head of the threaded rod has two of the at least one head limiting surface and two head arced surfaces, the two head limiting surfaces are respectively aligned with the two cavity limiting surfaces, and the two head arced surfaces are connected with the two head limiting surfaces, are arranged opposite to each other, and are respectively aligned with the two cavity arced surfaces; and the threaded rod has two of the multiple engaging protrusions respectively protruding from the two head arced surfaces and respectively engaged with the two engaging grooves.

9. The vaginal speculum as claimed in claim 8, wherein;
a diameter of a circumscribed circle of the rod hole is smaller than a diameter of a circumscribed circle of the insertion cavity;
a through hole is formed through the first handle; and
the rod of the threaded rod extends through the through hole in the first handle and extends out from the first handle.

* * * * *